United States Patent [19]

Regan et al.

[11] Patent Number: 4,843,081
[45] Date of Patent: Jun. 27, 1989

[54] ARYL AND HETEROARYL SUBSTITUTED CYCLOALKYL COMPOUNDS

[75] Inventors: John R. Regan, Princeton, N.J.; Jeffrey N. Barton, Philadelphia; John T. Suh, Maple Glen, both of Pa.; Jerry W. Skiles, Tuckahoe, N.Y.

[73] Assignee: Rorer Pharmaceutical Corporation, Fort Washington, Pa.

[21] Appl. No.: 213,043

[22] Filed: Jun. 27, 1988

Related U.S. Application Data

[60] Division of Ser. No. 732,557, Nov. 20, 1986, Pat. No. 4,795,757, which is a continuation-in-part of Ser. No. 646,735, Sep. 4, 1984, abandoned.

[51] Int. Cl.$^4$ ............... A61K 31/47; C07D 217/04
[52] U.S. Cl. ............................ 514/307; 514/183; 514/210; 514/212; 514/215; 514/311; 514/314; 514/414; 514/415; 514/416; 540/476; 540/594; 546/145; 546/147; 546/148; 546/149; 546/150; 546/165; 548/458; 548/466; 548/482; 548/490; 548/491; 548/494; 548/505; 548/506; 548/509
[58] Field of Search ............... 546/145, 147, 148, 149, 546/150, 165; 548/458, 466, 482, 490, 491, 494, 505, 506, 509, 950; 514/307, 311, 314, 414, 416, 415, 183, 210, 212, 215; 540/476, 594

[56] References Cited

PUBLICATIONS

Cantarelli et al., "Chemical Abstracts", vol. 73, 1970, col. 2397r.
Unger et al., "Chemical Abstracts", vol. 79, 1973, col. 65987c.

*Primary Examiner*—Glennon H. Hollrah
*Assistant Examiner*—James H. Turnipseed

[57] ABSTRACT

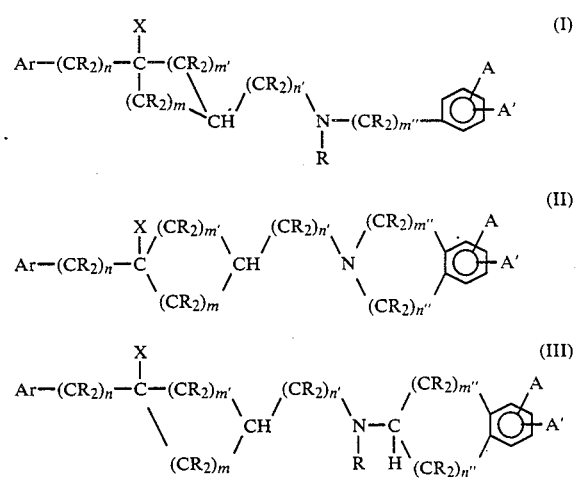

and pharmaceutically acceptable salts thereof, wherein:
Ar is phenyl, naphthyl, heteroaryl, indole, or fused arylcycloalkyl optionally substituted with hydroxy, halo, $CF_3$, $NO_2$, $C_{1-6}$ alkyl, $C_{1-6}$ alkoxy or aryloxy;
A and A' are each hydrogen, $C_{1-6}$ alkyl, $C_{1-6}$ alkoxy, hydroxy or aryloxy;
X is cyano, nitro, COOR, SR, SOR or SOOR;
R is H, $C_{1-6}$ alkyl or aryl;
n n' and n" are each 0 to 4; and
m, m' and m" are each 1 to 4, have calcium channel blocking activity.

4 Claims, No Drawings

ARYL AND HETEROARYL SUBSTITUTED CYCLOALKYL COMPOUNDS

This application is a division of copending application Ser. No. 932,557, filed on Nov. 20, 1986, now U.S. Pat. No. 4,795,757, which in turn is a continuation-in-part of application Ser. No. 646,735, filed Sept. 4, 1984, now abandoned.

This invention relates to bisarylamines. More particularly, it relates to bisarylamines which possess antihypertenisve, vasodilating, and calcium channel blocking activity, a process for the preparation thereof, and to pharmaceutical composition comprising the same for thereapeutical treatment of cardiovascular diseases.

The new compounds of the present invention have the formulae:

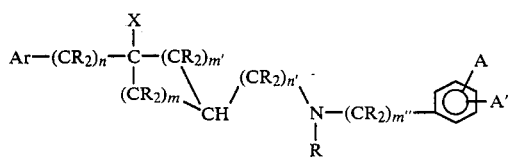
(I)

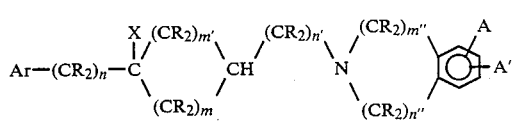
(II)

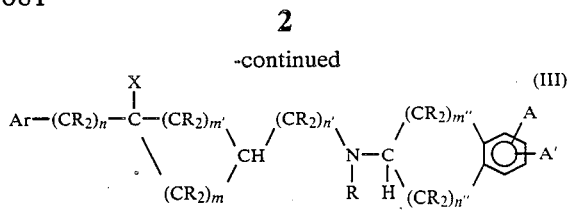
(III)

and pharmaceutically acceptable salts thereof, wherein:

Ar is phenyl, naphthyl, heteroaryl, indole, or fused arylcycloalkyl optionally substituted with hydroxy, halo, $CF_3$, $NO_2$, $C_{1-6}$ alkyl, $C_{1-6}$ alkoxy or aryloxy;

A and A' are each hydrogen, $C_{1-6}$ alkyl, $C_{1-6}$ alkoxy, hydroxy or aryloxy;

X is cyano, nitro, COOR, SR, SOR or SOOR;

R is H, $C_{1-6}$ alkyl or aryl;

n, n' and n" are each 0 to 4; and m, m' and m" are each 1 to 4.

The term heteroaryl includes pyridyl, pyrimidyl, pyridazinyl, quinolinyl, isoquinolinyl, furanyl, thiophenyl, quinoxalinyl and indolyl; while the term fused arylcycloalkyl includes tetrahydroisoquinolinyl, tetrahydroquinolinyl, indanyl, tetrahydroquinoxalinyl, tetrahydronaphthalene, dihydroindolyl and dihydrobenzofuran.

The present new compounds are readily preparable by art-recognized procedures. Starting materials may be obtained from commercial sources, or may be prepared by known synthetic methods.

A particularly effective synthetic method is illustrated schematically, using the starting materials denoted by A. (obtained from Aldrich Chem. Co.) and the reactant B. (as described by F. Buck, *J. Amer. Chem. Soc.* 1769 (1934).

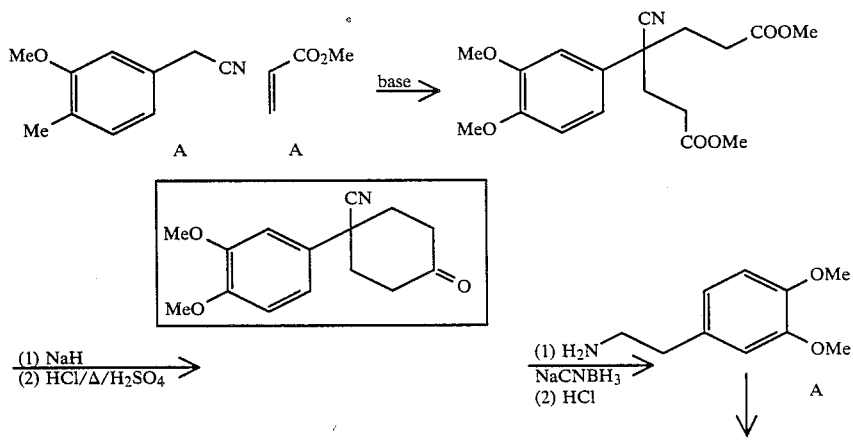

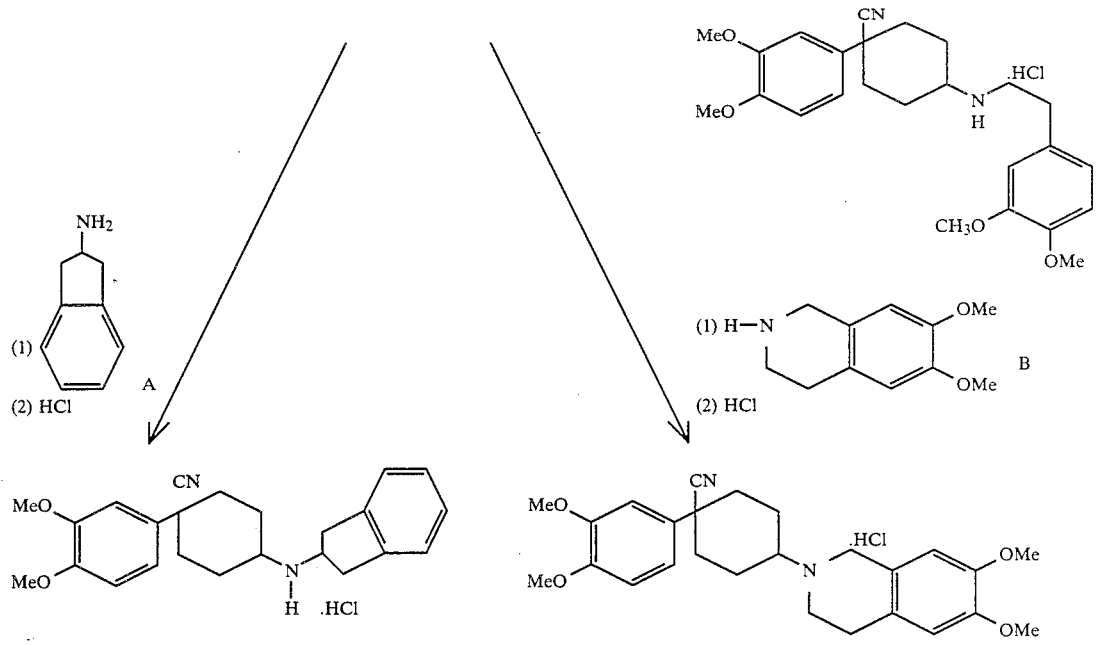

Compounds of the present invention possess calcium channel blocking activity and as such are useful for the treatment of cardiovascular diseases, such as, angina pectoris, coronary spasm, arrythmias, arterial and pulmonary hypertension, myocardial infarction and cerebral vasospasm.

Compositions of this invention comprise, as an active ingredient, an effective amount of a compound according to the present invention in a pharmaceutically acceptable carrier.

In general, the substance of this invention is administered in analogy to known, commercially available formulations with a similar indication in dosages of approximately 1 to 200 mg per dosage unit or higher. The daily dosage is approximately 0.02–5 mg/kg of body weight. It is to be understood, however, that the particular dose for each patient as usual depends on very diverse factors, such as the age, body weight, general condition of health, sex, diet, and the like of the patient, on the time and route of administration, or the rate of excretion, on the combination of medicaments and on the severity of the particular disease to which therapy relates.

The compounds of the present invention may be administered enterally, parenterally or topically. The compounds may be incorporated into pharmaceutical formulations having excipients suitable for these administrations and which do not adversely react with the compound, for example, water vegetable oils, certain alcohols and carbohydrates, gelatin, magnesium stearate, talc, cornstarch or petroleum jelly. The pharmaceutical formulations containing an active compound of the present invention may be made into: tablets, capsules, elixirs, drops or suppositories for enteral administration; solutions, suspensions or emulsions for parenteral administration; ointments, creams or powders for topical application, and inhalation capsules, sprays, nasal and eye drops.

The following examples will further illustrate the invention:

EXAMPLE 1

Dimethyl 4-(3,4-dimethoxyphenyl)-4-cyanopimelate

To a solution of (3,4-dimethoxyphenyl)acetonitrile (20.0 g, 0.113 mol), methyl acrylate (22.9 ml, 0.254 mol) in 500 ml t-butanol at 65° C. was added dropwise Triton B (6 g of a 40% methanol solution) in 12 ml t-butanol. The mixture was heated at reflux for 3 hours and the volatiles were removed in vacuo. The residue was diluted with ethyl acetate, washed with water, sodium bicarbonate, dilute HCl, and brine and dried using MgSO$_4$. The volatiles were removed in vacuo which left a residue that was purified by HPLC using 33% ethyl acetate in hexanes as eluents, mp 72°–3° C.

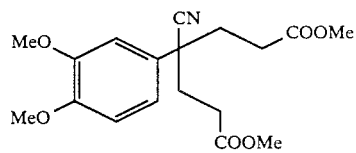

EXAMPLE 2

4-(3,4-Dimethoxyphenyl)-4-cyanocyclohexanone

A solution of dimethyl 4-(3,4-dimethoxyphenyl)-4-cyanopimelate (11.2 g, 32.1 mmol), sodium hydride (2.31 g, 48.1 mmol) and methanol (1 ml) in 250 ml anhydrous toluene was heated at reflux for 10 hours, cooled to 25° C., quenched with 4 ml acetic acid, washed with H$_2$O, alkali, and brine and dried with MgSO$_4$. The volatiles were removed in vacuo. The residue was recrystallized with hexanes-ethyl acetate. This intermediate was heated at reflux in ethanol, concentrated HCl and 25% aqueous H$_2$SO$_4$ for 10 hours. The volatiles were removed in vacuo. The residue was diluted with water and extracted with ether. The combined organic extracts were washed with water, brine and dried (MgSO$_4$). The volatiles were removed in vacuo. The residue was recrystallized with toluene and then with hexanes-ethyl acetate, mp 111°-12° C.

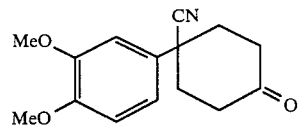

EXAMPLE 3

N-[2-(3,4-Dimethoxyphenyl)ethyl]-4-cyano-4-(3,4-dimethoxyphenyl)-1-aminocyclohexane Hydrochloride A solution of 4-(3,4-dimethoxyphenyl)-4-cyanocyclohexanone (1.07 g, 4.13 mmol), β-(3,4-dimethoxyphenyl)ethylamine (0.748 g, 4.13 mmol) and sodium cyanoborohydride (0.285 g, 4.54 mmol) in 15 ml ethanol was stirred 18 hours and the volatiles were removed in vacuo. The residue was dissolved in ethyl acetate, washed with water, saturated sodium bicarbonate and brine, and dried (MgSO4) and the volatiles were removed in vacuo. The residue was diluted with 1:1 ether:ethyl acetate and anhydrous HCl was added. The solid was filtered and recrystallized with aqueous ethanol which provided the product, m.p. >250° C.

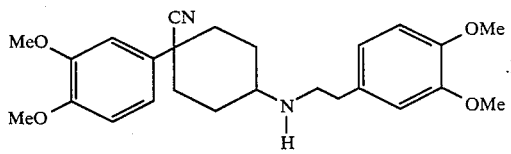

EXAMPLE 4

N-[2-(3,4-Dimethoxyphenyl)ethyl]-N-Methyl-4-cyano-4-(3,4-dimethoxyphenyl)-1-aminocyclohexane Hydrochloride A solution of 4-(3,4-dimethoxyphenyl)-4-cyanocyclohexanone (4 mmol), N-methyl-β-(3,4-dimethoxyphenyl)ethylamine, prepared from β-(3,4-dimethoxyphenyl)ethylamine, formaldehyde and formic acid, (4 mmol) and sodium cyanoborohydride in 15 ml isopropanol was stirred at 25° C. for 72 hours, poured onto ice water and extracted with ethyl acetate. The product was prepared by adding anhydrous HCl and recrystallization from aqueous ethanol.

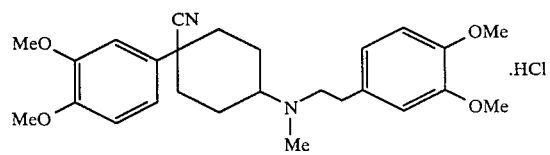

EXAMPLE 5

N-[4-(3,4-Dimethoxyphenyl)butyl]-N-(1-methylethyl)-4-cyano-4-(3,4-dimethoxyphenyl)-1-aminocyclohexane Hydrochloride A solution of 4-(3,4-dimethoxyphenyl)-4-cyanocyclohexane (5 mmol), N-(1-methylethyl)-4-(3,4-dimethoxyphenyl)butylamine hydrochloride (5 mmol), triethylamine (6 mmol) and sodium cyanoborohydride (6 mmol) in 25 ml ethanol was stirred at 25° C. for 72 hours and worked up and recrystallized.

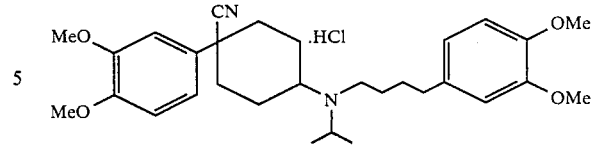

Using appropriate starting materials and analogous procedures to those of Examples 1-5, the following compounds were made:

EXAMPLE 6

N-[2-(3,4-Dimethoxyphenyl)ethyl]-3-cyano-3-(3,4-dimethoxyphenyl)-1-aminocyclohexane

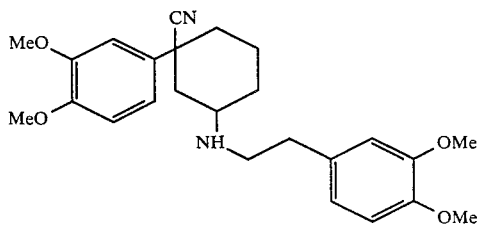

EXAMPLE 7

N-[4-(3,4-Dimethoxyphenyl)butyl]-N-phenyl-4-cyano-4-(3,4-dimethoxyphenyl)-1-aminocyclohexane

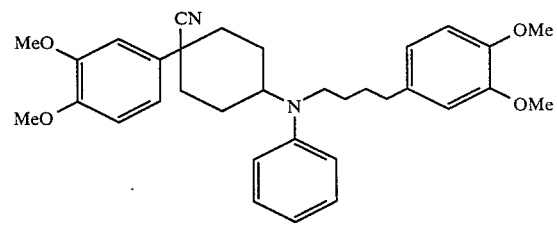

EXAMPLE 8

N-[2-(3,4-dimethoxyphenyl)ethyl]-N-methyl-5cyano-5-(3,4-dimethoxyphenyl)-1-aminocyclooctane

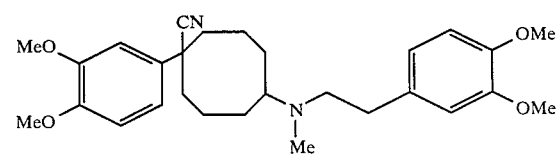

EXAMPLE 9

N-[2-(3,4-dimethoxyphenyl)ethyl]-N-methyl-4-cyano-4-(3-hydroxy-4-methoxyphenyl)-1-aminocyclohexane

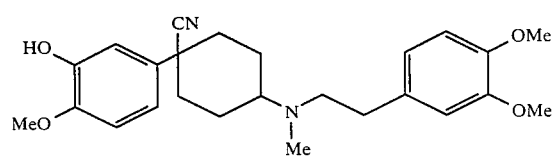

EXAMPLE 10

N-[4-(3,4-Dimethoxyphenyl)-4-cyanocyclohexan-1-yl]-
6,7-dimethoxy-1,2,3,4-tetrahydroisoquinoline
Hydrochloride A solution of 4-(3,4-dimethoxyphenyl)-4-cyanocyclohexanone (1.64 g, 6.33 mmol), 6,7-dimethoxy-1,2,3,4-tetrahydroisoquinoline (1.16 g, 6.01 mmol) and sodium cyanoborohydride (0.596 g, 9.50 mmol) in 25 ml isopropanol was stirred at 25° C. for 47 hours, poured onto water and extracted with ethyl acetate. The combined organic layers were washed with 1N NaOH and brine and dried (MgSO4) and the volatiles were removed in vacuo. The residue was treated with ethanol and anhydrous HCl and the volatiles were removed in vacuo. The solid was recrystallized with aqueous ethanol which provided the product, mp >250° C.

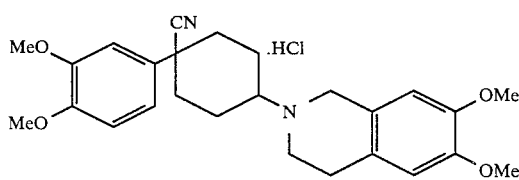

EXAMPLE 11

N-[4-(3,4-Dimethoxyphenyl)-4-cyanocyclohexan-1-yl]-
5-methoxy-2,3-dihydroindole Hydrochloride A solution of 4-(3,4-dimethoxyphenyl)-4-cyanocyclohexanone (5.5 mmol) 5-methoxy-2,3-dihydroindole hydrochloride (5.5 mmol), triethylamine (6.0 mmol) and sodium cyanoborohydride (5.5 mmol) in 30 ml isopropanol was stirred at 25° C. for several days, poured onto ice water and extracted with ethyl acetate. The organic layers were washed with alkali, dried (MgSO4) and the volatiles were removed in vacuo. The salt of the product was prepared from anhydrous HCl in ethyl acetate.

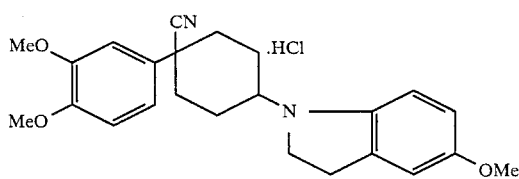

EXAMPLE 12

N-[4-(3,4-Dimethoxyphenyl)-4-cyanocyclohexan-1-yl]-
6,7-dimethoxy-1,2,3,4-tetrahydroquinoline
Hydrochloride A solution of 4-(3,4-dimethoxyphenyl)-4-cyanocyclohexanone (3.5 mmol), triethylamine (3.5 mmol), 6,7-dimethoxy-1,2,3,4-tetrahydroquinoline hydrochloride (3.5 mmol) and sodium cyanoborohydride (5 mmol) in 50 ml iso-propanol was stirred at 25° C. for several days, poured onto ice water and extracted with ethyl acetate. The salt was prepared from anhydrous HCl in ethyl acetate.

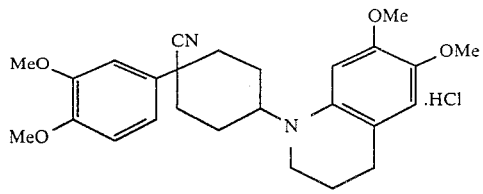

Using appropriate starting materials and analogous procedures to those of Examples 10–12, the following compounds were made:

EXAMPLE 13

N-[3-(3,4-Dimethoxyphenyl)-3-cyanocyclohexan-1-yl]-
6,7-dimethoxy-1,2,3,4-tetrahydroisoquinoline

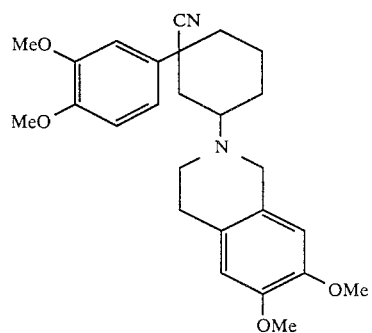

EXAMPLE 14

N-[3-(3,4-Dimethoxyphenyl)-3-cyanocyclohexan-1-yl]-
6,7-dimethoxy-1,2,3,4-tetrahydroquinoline

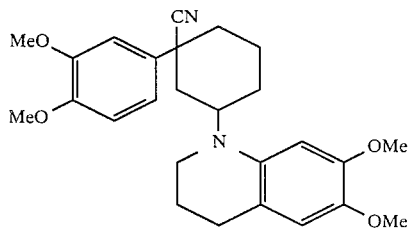

EXAMPLE 15

N-[5-(3,4-Dimethoxyphenyl)-5-cyanocyclooctan-1-yl]-
6,7-dimethoxy-1,2,3,4-tetrahydroisoquinoline

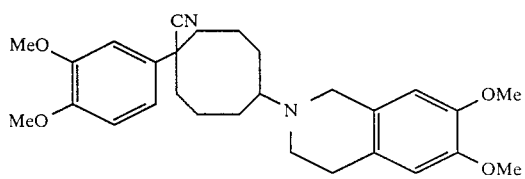

EXAMPLE 16

N-[3-(3-methoxy-4-hydroxyphenyl)-3-cyanocyclopentan-1-yl]-5,6-dimethoxy-2,3-dihydroindole

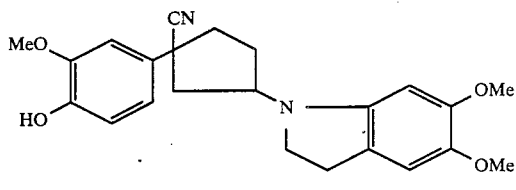

EXAMPLE 17

N-(2,3-Dihydro-1H-inden-2-yl)-4-(3,4-dimethoxyphenyl)-4-cyano-1-aminocyclohexane Hydrochloride A solution of 4-(3,4-dimethoxyphenyl)-4-cyanocyclohexanone (0.71 g, 2.74 mmol), triethylamine (0.38 ml, 2.74 mmol), 2-amino-2,3-dihydro-1H-inden hydrochloride (0.46 g, 2.74 mmol) and sodium cyanoborohydride (0.17 g, 2.7 mmol) in 10 ml ethanol was stirred at 25° C. for 3 days, filtered and the volatiles were removed in vacuo. The residue was diluted with ethyl acetate, washed with water, 1N NaOH and brine and dried (MgSO$_4$). The volatiles were removed in vacuo. The residue was treated with ethyl acetate and anhydrous HCl. The volatiles were removed in vacuo. Recrystallization of the residue with aqueous ethanol gave the product, m.p. >250° C.

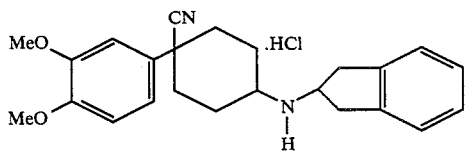

EXAMPLE 18

N-(2,3-Dihydro-1H-inden-1-yl)-N-methyl-4-(3,4-dimethoxyphenyl)-4-cyano-1-aminocyclohexane Hydrochloride A solution of 4-(3,4-dimethoxyphenyl)-4-cyanocyclohexanone (5 mmol), triethylamine (5 mmol), 1-methylamino-2,3-dihydro-1H-inden hydrochloride (5 mmol) and sodium cyanoborohydride (5 mmol) in 20 ml ethanol was stirred at 25° C. for 3 days and worked up as in Example 17. The hydrochloride salt was prepared with anhydrous HCl in ethyl acetate.

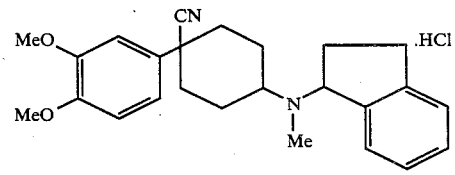

EXAMPLE 19

N-(1,2,3,4-Tetrahydronaphthalen-2-yl)-N-ethyl-4-(3,4-dimethoxyphenyl)-4-cyano-1-aminocyclohexane Hydrochloride A solution of 4-(3,4-dimethoxyphenyl)-4-cyanocyclohexanone (3 mmol), triethylamine (3 mmol), 2-ethylamino-1,2,3,4-tetrahydronaphthalene hydrochloride prepared by reductive amination of 3,4-dihydro-2-(1H)-naphthalenone with ethylamine and sodium cyanoborhydride, (3 mmol) in ethanol was stirred 72 hours and worked up as in Example 17.

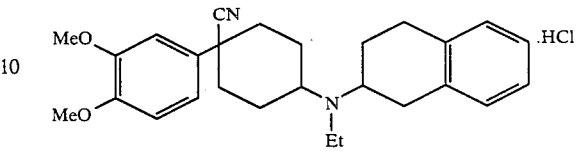

Using appropriate starting materials and analogous procedures to those of Examples 17–19, the following compounds were made:

EXAMPLE 20

N-(2,3-Dihydro-1H-inden-2-yl)-N-methyl-5-(3,4-dimethoxyphenyl)-5-cyano-1-aminocyclooctane

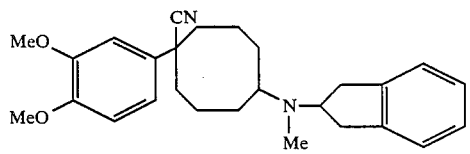

EXAMPLE 21

N-(6,7-Dimethoxy-1,2,3,4-tetrahydronaphthalen-1-yl)-N-methyl-3-(3,4-dimethoxyphenyl)-3-cyano-1-aminocyclohexane

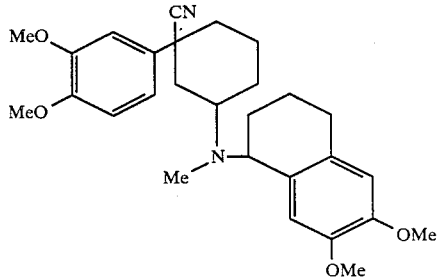

EXAMPLE 22

N-(5,6-Dimethoxy-2,3-dihydro-1H-inden-2-yl)-N-methyl-3-(3-hydroxy-4-methoxyphenyl)-3-cyano-1-aminocyclohexane

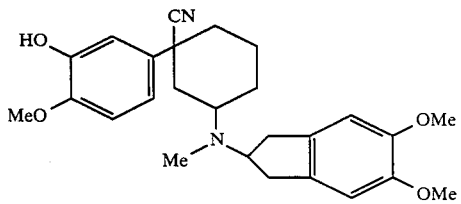

EXAMPLE 23

N-[4-Cyano-4-[2-(3,4-dimethoxyphenyl)ethyl]cyclohexanyl]-6,7-dimethoxy-1,2,3,4-tetrahydroisoquinoline

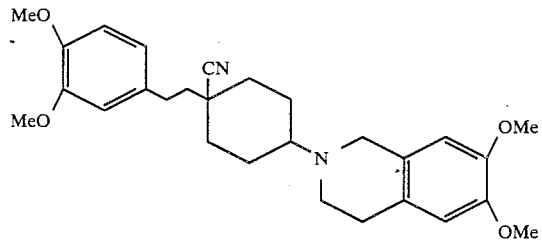

EXAMPLE 24

5-[N-Methyl-N-[2-(3,4-dimethoxyphenyl)ethyl]ethylamino]-1-(3,4-dimethoxyphenyl)cyclooctanenitrile

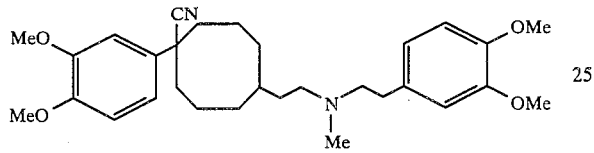

Compounds of the present invention were tested by the procedure that follows, which is essentially based on the procedure described by J. R. Weeks and J. A. Jones, *Proc. Soc. Exp. Biol. Med.*, 104, 646 (1960).

Fourteen week old, male spontaneously hypertensive rats (SHR) (Charles River Breeding Laboratories, Wilmington, MA), weighing 195–240 g, were used. They were maintained on a low-sodium diet (100 ppm, ICN Pharmaceuticals, Cleveland OH) and distilled water for 2 weeks prior to use in order to elevate their plasma renin activities. Seven days prior to the experiments, polyethylene catheters were implanted in their abdominal aortae under ether anesthesia. On the day of experimentation, the rats were harnessed and their catheters were attached to a recording system via swivels that allowed the animals to roam freely within individual cages while their arterial pressures were monitored. Two rats were given each test compound by gavage and post-dosing arterial pressures were compared to the average arterial pressures during the half-hour just prior to dosing.

Representative results are shown for the following compounds:

At 100 mg/kg/i.p. administration to SHR of N-[2-(3,4-dimethoxyphenyl)ethyl]-4-cyano-4-(3,4-dimethoxyphenyl)-1-aminocyclohexane hydrochloride there was an 18–19% decrease in arterial pressure lasting for about 10 hours; while 100 mg/kg i.p. administration to SHR of N-[4-(3,4-dimethoxyphenyl]-4-cyanocyclohexan-1-yl)-6,7-dimethoxy-1,2,3,4-tetrahydroisoquinoline hydrochloride resulted in a 30–32% decrease in arterial pressure with a duration of 2.5 to 8 hours.

What is claimed is:

1. A member of the formula:

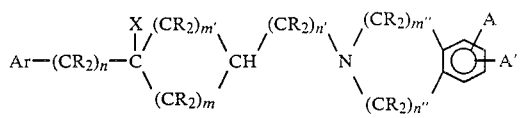

and pharmaceutically acceptable salts thereof, wherein:

Ar is phenyl, naphthyl, or indole optionally substituted with hydroxy, halo, $CF_3$, $NO_2$, $C_{1-6}$ alkyl or $C_{1-6}$ alkoxy;

A and A' are each hydrogen, $C_{1-6}$ alkyl, $C_{1-6}$ alkoxy, or hydroxy;

X is cyano, nitro, COOR, SR, SOR or SOOR;

R is H or $C_{1-6}$ alkyl;

n, n' and n" are each 0 to 4; and m, m' and m" are each 1 to 4.

2. A pharmaceutical composition for the treatment of cardiovascular diseases comprising as an active ingredient a member of the formula:

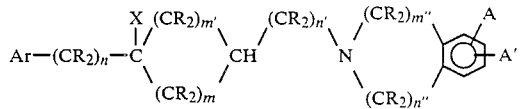

wherein:

Ar is phenyl, naphthyl, or indole optionally substituted with hydroxy, halo, $CF_3$, $NO_2$, $C_{1-6}$ alkyl or $C_{1-6}$ alkoxy;

A and A' are each hydrogen, $C_{1-6}$ alkyl, $C_{1-6}$ alkoxy or hydroxy;

X is cyano, nitro, COOR, SR, SOR or SOOR;

R is H or $C_{1-6}$ alkyl;

n, n' and n" are each 0 to 4; and m, m' and m" are each 1 to 4 or pharmaceutically acceptable salts thereof in a pharmaceutically acceptable carrier.

3. A method for effecting vasodilation in a mammal in need of such treatment which comprises administering thereto an effective amount of the composition of claim 2.

4. N-[4-(3,4-dimethoxyphenyl)-4-cyanocyclohexan-1-yl]-6,7-dimethoxy-1,2,3,4-tetrahydroisoquinoline hydrochloride.

* * * * *